(12) United States Patent
Hayes et al.

(10) Patent No.: US 6,591,702 B2
(45) Date of Patent: Jul. 15, 2003

(54) METHOD FOR IDENTIFYING SOURCES OF RAPIDLY RELEASED CONTAMINANTS AT CONTAMINATED SITES

(75) Inventors: Thomas D. Hayes, Schaumberg, IL (US); Vipul J. Srivastava, Woodridge, IL (US)

(73) Assignee: Gas Technology Institute, Des Plaines, IL (US)

( * ) Notice: Subject to any disclaimer, the term of this patent is extended or adjusted under 35 U.S.C. 154(b) by 0 days.

(21) Appl. No.: 10/005,310

(22) Filed: Dec. 3, 2001

(65) Prior Publication Data

US 2002/0103601 A1 Aug. 1, 2002

Related U.S. Application Data

(60) Provisional application No. 60/251,151, filed on Dec. 4, 2000.

(51) Int. Cl.[7] .................. G01N 33/00; G01N 33/24; E21B 44/00
(52) U.S. Cl. .................. 73/866; 73/152.43; 436/29
(58) Field of Search .................. 73/866, 19.09, 73/152.43, 863.11; 175/17, 50; 435/9; 436/25, 28, 29, 31

(56) References Cited

U.S. PATENT DOCUMENTS

| | | | | |
|---|---|---|---|---|
| 2,165,440 A | * | 7/1939 | Bays | 436/29 |
| 2,183,964 A | * | 12/1939 | Horvitz | 436/29 |
| 2,305,384 A | * | 12/1942 | Hoover | 436/28 |
| 2,349,472 A | * | 5/1944 | Taggart | 435/9 |
| 2,386,832 A | * | 10/1945 | Zaikowsky | 73/863.11 |
| 2,725,281 A | * | 11/1955 | Bond | 436/31 |
| 2,918,579 A | * | 12/1959 | Slobod | 250/255 |
| 3,033,761 A | * | 5/1962 | Brown | 435/9 |
| 3,120,428 A | * | 2/1964 | McDermott | 436/29 |
| 3,180,983 A | * | 4/1965 | Hall | 250/255 |
| 3,307,912 A | * | 3/1967 | Davis | 436/29 |
| 4,573,354 A | * | 3/1986 | Voorhees et al. | |
| 4,809,790 A | * | 3/1989 | Manchak, Jr. | 175/17 |
| 4,834,194 A | * | 5/1989 | Manchak, Jr. | 175/50 |
| 5,063,519 A | | 11/1991 | Zison | |
| 5,137,830 A | * | 8/1992 | Milly | 436/25 |
| 5,328,849 A | | 7/1994 | Smith | |
| 5,435,176 A | * | 7/1995 | Manchak, III | 73/152.43 |
| 5,687,093 A | | 11/1997 | Long et al. | |
| 5,766,953 A | | 6/1998 | Kennedy | |
| 5,813,798 A | | 9/1998 | Whiffen | |
| 5,862,512 A | | 1/1999 | Voorhees et al. | |
| 5,873,049 A | | 2/1999 | Bielak et al. | |
| 5,905,036 A | | 5/1999 | Pope et al. | |
| 6,035,701 A | * | 3/2000 | Lowry et al. | 73/40.7 |
| 6,128,577 A | | 10/2000 | Assa et al. | |
| 6,169,962 B1 | | 1/2001 | Brookshire et al. | |

* cited by examiner

Primary Examiner—Helen Kwok
Assistant Examiner—Jay L Politzer
(74) Attorney, Agent, or Firm—Mark E. Fejer (57) ABSTRACT

A method for identifying and characterizing contaminated sources in a site having contaminated soils and sediments in which vapor pressure is measured at a plurality of subsurface soil sampling locations of the site, which measurements are then mapped, resulting in generation of a subsurface vapor pressure map. Contaminant mobility at the subsurface soil sampling locations having a peak vapor pressure is then determined and contaminants in fast release compartments and slow release compartments in the contaminated soils and sediments identified. Thereafter, the fraction of contaminants in the fast release compartments and the slow release compartments is determined. Calibration of the contaminant-specific vapor pressure with laboratory measurements of the rapid release fraction at each site allows a meaningful and rapid estimation of the spatial location and mass distribution of source areas.

9 Claims, 4 Drawing Sheets

SCHEMATIC OF VAPOR PRESSURE CHARACTERIZATION OF A CONTAMINATED SITE (EXAMPLE)

METHOD FOR IDENTIFYING SOURCES OF RAPIDLY RELEASED CONTAMINANTS AT CONTAMINATED SITES

CROSS-REFERENCE TO RELATED APPLICATION

This application claims the benefit of Provisional application Serial No. 60/251,151 filed Dec. 4, 2000.

BACKGROUND OF THE INVENTION

1. Field of the Invention

This invention relates to a method for characterizing contaminated soils and sediments so as to permit timely determination of the likely sources of rapidly released fractions of contaminants disposed in the contaminated soils and sediments, thereby enabling accurate decisions to be made as to the soils and sediments needing to be removed and/or treated to achieve risk-based cleanup objectives. The method is sufficiently rapid to enable decisions to be made in the course of excavating a contaminated site.

2. Description of Related Art

The characterization of contaminated industrial and governmental sites can involve significant costs due to the inability to define "source" when used in describing sources of contaminants that significantly contribute to the degradation of groundwater, the inadequacy of current methods for measuring the fraction of contaminants that are available for transport to receptors such as groundwater, and the long lead times of days or weeks required for contaminant measurements to be obtained from commercial laboratories. These limitations prevent the timely definition of what constitutes a problematic source of contaminants at each site which would allow site managers to define which volumes of soil require aggressive treatment or removal and which soils are not an issue in terms of significant impact on receptors. Consequently, characterization costs of up to millions of dollars per site can be incurred without a true definition of source in terms of contaminant release rates, as a further result of which large volumes of soil are unnecessarily excavated and/or treated at substantial costs to the site owners.

Current methods for determining which volumes of soil are sources of contaminants and which soils are not range from the over-simplistic to the analytical approaches that require very long lead times of several days or weeks. One such method involves the determination of total concentrations of contaminants of concern. However, this type of data is of limited use in predicting the rates of contaminant release from various sections of the site. At such sites, decisions regarding cleanup levels and the planned removal and/or treatment of soil/NAPL (non-aqueous phase liquids) residues are guided by the total concentrations of the contaminants of concern. This results in a gross over-estimation of the volumes of soil/NAPL residues that are identified as "source" for contaminants and that are subsequently targeted for aggressive management.

Other methods currently in use are visual observations of staining believed to be due to hydrocarbon impact and olfactory detection of contaminants through "hydrocarbon" odor. However, visual and olfactory observations, as shown in Table 1 hereinbelow, are not good predictors of the potential of a soil/NAPL residue to impact groundwater or to become available to other receptors. Total concentration is also a poor indicator of contaminant availability to receptors.

TABLE 1

Comparisons of Vapor Pressure (PID) Measurements, Visual Observations and Olfactory Determinations with Impact to Groundwater
(Benzene Levels in Water Partitioned with Soil)
Source Groundwater Impact Characterization Data

| Sample | Depth, feet | New PID | Old PID | Initial Benzene Soil, mg/kg | Water* mg/l | **Benzene Loss in Soil leach columns, mg/kg | **Benzene & Naphthalene Loss in soil leach columns, mg/kg | *Old Observations | Groundwater Impact |
|---|---|---|---|---|---|---|---|---|---|
| SB1-03 | 6–8 | 9–40 | 87 | 1.14 | .0007 | 1.01 | 1.58 | HC Stained/odor | Minimal |
| SB1-03 | 9–11 | 0–22 | ~50 | 0.78 | .0009 | 0.67 | 1.98 | HC Stained/odor | Minimal |
| SB-62 | 10–12 | 9–49 | no data | 0.28 | .0056 | 0.27 | 0.51 | No observation | Minimal |
| SB-62 | 15.5–17.5 | 8–24 | no data | 1.47 | .0036 | 1.47 | 21.37 | 15–16 ft no observations 17 ft tar observed | Minimal |
| SB-59 | 4–6 | 65–177 | 101 | 7.44 | .007 | 5.62 | 86.66 | MGP-like odor with staining at 0.8 ft from bottom | Minimal |
| SB-59 | 18–20 | 189–480 | 400 | 340 | 3.08 | 209.48 | 1528.00 | MGP-like odor with | High |

TABLE 1-continued

Comparisons of Vapor Pressure (PID) Measurements, Visual
Observations and Olfactory Determinations with Impact to Groundwater
(Benzene Levels in Water Partitioned with Soil)
Source Groundwater Impact Characterization Data

| Sample | Depth, feet | New PID | Old PID | Initial Benzene Soil, mg/kg | Initial Benzene Water* mg/l | **Benzene Loss in Soil leach columns, mg/kg | **Benzene & Naphthalene Loss in soil leach columns, mg/kg | *Old Observations | Groundwater Impact |
|---|---|---|---|---|---|---|---|---|---|
| | | | | | | | | visual product from 1.7 ft to bottom | |

*Tap water in equilibrium with soil: 30 g soil + 100 ml tap water
**Losses from disturbed soils in leach columns calculated from containment concentration before and after leaching with 150 pore volumes of tap water It is, thus, apparent that there is a need for a method which provides reliable and rapid means for defining what soil/NAPL residues constitute significantly available sources of contaminants at contaminated sites.

SUMMARY OF THE INVENTION

It is, thus, one object of this invention to provide a method for defining soil/NAPL residues that constitute significantly available sources of contaminants at contaminated sites.

It is another object of this invention to provide a method for defining sources of contaminants in contaminated soils and sediments that significantly contribute to the degradation of groundwater and other contaminant receptors.

It is yet a further object of this invention to provide a method for measuring the fraction of contaminants in contaminated soils and sediments that are available for transport to receptors such as groundwater.

It is still a further object of this invention to provide a method for defining sources of contaminants in contaminated sites that reduces the amount of time required for obtaining such information in comparison to the days and weeks required by conventional methods.

It is yet a further object of this invention to provide a rapid method of estimating the mass of rapidly released hydrocarbon contaminants in each section of a site so as to quantify the spatial mass distribution of significant sources of rapidly released contaminants.

It is a further object of this invention to provide a method for defining sources of contaminants in contaminated sites that can be carried out at such contaminated sites.

These and other objects of this invention are addressed by a method for identifying and characterizing contaminated sources in a site comprising contaminated soils and sediments in which the vapor pressure at a plurality of subsurface soil sampling locations of the site is measured, producing a plurality of subsurface vapor pressure measurements with depth, which measurements are then mapped, resulting in generation of a subsurface vapor pressure map. The vapor pressure mapping indicates the spatial distribution of the total mass of rapidly releasable contaminants.

Commercially available instrumentation that provides contaminant-specific vapor pressures would yield a mapping of the rapidly releasable mass of only a specific contaminant. Concomittently, soil samples are analyzed in the laboratory for contaminant mobility using mobility test procedures such as the Synthetic Precipitation Leaching Procedure (SPLP), leaching tests and resin enhanced desorption of the soil. The results of these tests may be used to calibrate vapor pressure instrumentation. Using vapor pressure measurements together with total concentration measurements, contaminants in fast release compartments and slow release compartments in the contaminated soils and sediments are identified and the fraction of the contaminants in the fast release compartments and the slow release compartments rapidly determined in the field.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

The invention disclosed and claimed herein is a procedure that embodies a screening method for determining the areas of a contaminated site that represent the rapid release of contaminants of concern. This invention includes a number of essential elements of know-how, analytical testing and data analysis that enable a screening tool to be calibrated and used for each site with a high degree of reliability. The screening tool facilitates decisions having to do with whether or not a volume of soil has the potential to substantially contribute to the release of a contaminant of concern to groundwater and/or other receptors, such as ecological organisms, animals and humans.

The central premise of the method of this invention is that the vapor pressure of the volatile constituents of a contaminated soil is a good indicator of the true mobility (fugacity) of the volatile organic constituents in the environment. The tendency of a chemical to transfer to and from a gaseous environmental phase in the subsurface soil is determined by its vapor pressure. This property can be used to reflect the equilibrium distribution or the rates of exchange to and from the soil/NAPL complex. The primary problem is that many types of organic materials at contaminated sites exert a vapor pressure, both hazardous and non-hazardous constituents, including natural organic compounds such as methane. The measurement and interpretation of these vapor pressures to determine the potential for mobility of the contaminants of concern is the challenge that is addressed by the method of this invention.

As previously stated, the measurement of the total concentration of a contaminant in soil is a poor indicator of the mobility of that contaminant in the environment or its "availability" for transport to groundwater and other receptors. This is because most contaminants are bound to the complex of soil, natural organic matter and non-aqueous phase liquids (NAPL) in a manner that involves multiple mechanisms of binding and multiple types of binding sites. Upon contact with water, the release of a contaminant is consistent with a two-compartment release mode. One fraction of the contaminant is released rapidly and another fraction of the contaminant is released slowly. It is the rapid release fraction that is the portion of the contaminant that is "available" to receptors and that is the fraction that requires careful measurement and management in source areas of contaminated sites. The method of this invention, comprising a suite of vapor pressure measurement and contaminant mobility tests, represents a substantial improvement in providing a rapid and reliable measurement of the "available" fraction at contaminated sites that provides benefits of cost savings and improves decision-making in site management.

The total vapor pressure that is measured is the sum of the vapor pressures of all of the organic chemical constituents in the soil/NAPL complex.

$$\text{Total Vapor Pressure} = P_T = \sum_{i=0}^{i} P_i$$

where $P_i$=partial pressure of organic constituent i.

The vapor pressure of component i is a function of the concentrations of component i in the fast and slow release sorption compartments of the soil complex:

$$P_i = K_H * C_S^{i\text{-}rapid}/K_d^{i\text{-}rapid} + K_H * C_S^{i\text{-}slow}/K_d^{i\text{-}slow}$$

where:

$K_H$=Henry's Law constant for constituent i $C_S^{i\text{-}rapid}$=concentration of constituent in the soil complex that is in the rapid release compartment $C_S^{i\text{-}slow}$=concentration of constituent in the soil complex that is in the slow release compartment $K_d^{i\text{-}rapid}$=partitioning constant for the rapid release fraction of the constituent between soil and the water phases $K_d^{i\text{-}slow}$=partitioning constant for the slow release fraction of the constituent between soil and the water phases The partitioning constant, $K_d$, is defined by the ratio of the constituent concentrations in the soil and water.

$$K_d = C_W/C_S$$

where:

$C_W$=concentration of the constituent in water $C_S$=concentration of the constituent in the soil From the above equations, it can be seen that regardless of whether or not the soil/NAPL complex is in direct contact with the interstitial gases that are measured for vapor pressure and whether or not the soil/NAPL complex is enveloped in water, as is the case with many samples taken from sites with shallow water tables, the measurement of partial pressure is a reflection of the concentrations of the organic constituents in the soil. The total vapor pressure is a composite reflection of all constituents in all compartments of the soil. The more volatile the constituent is, the more influence it has on vapor pressure. The higher the volatile constituent concentration is, the larger the vapor pressure contribution. Not so obvious is the fact that the fraction of constituent in the fast release compartment has greater influence on vapor pressure than the same constituent in the slow release compartment, because the soil/water partitioning constant for the rapid release fraction is substantially less than the constant for the slow release fraction.

$$K_d^{i\text{-}rapid} << K_d^{i\text{-}slow}$$

Because this is true, the partial pressures are principally a measure of the constituents in the fast release compartment.

$$P_i = K_H * C_S^{i\text{-}rapid}/K_d^{i\text{-}rapid}$$

Hence, the total pressure measured in the field can be used as a screening indicator of the contaminants in the rapid release compartment of the soil complex.

Figure 1:
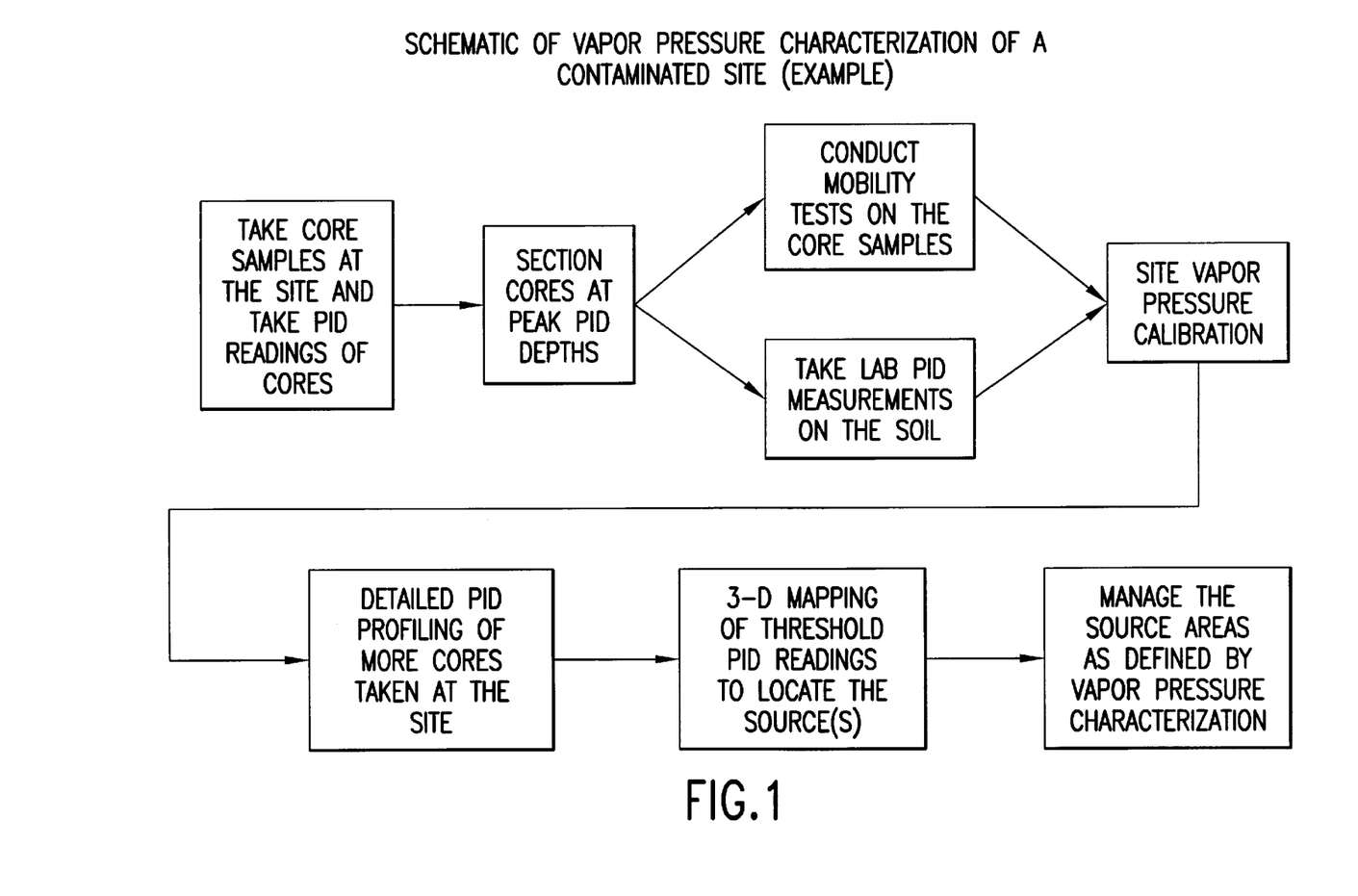
FIG. 1 is a conceptual schematic diagram showing the method of this invention.

The method of this invention comprises a combination of laboratory analytical procedures to determine the rapid and slow release fractions in soils, methodology for in-field vapor pressure measurements, and a procedure that correlates the data between the laboratory measurements and the field measurements of vapor pressures. This site-specific information is used to calibrate a computer screening model that allows rapid determinations of the location of rapid-contaminant-release source areas based upon vapor pressure profiles and field measurements. A conceptual schematic diagram showing the steps of the method of this invention is shown in FIG. 1. Although indicating the use of a photoionization detector (PID) for measuring total vapor pressures in soil/NAPL samples, it will be apparent to those skilled in the art that other valid analytical vapor measurement procedures may be substituted for the PID.

The first step in accordance with the method of this invention is to measure the vapor pressure at a plurality of subsurface soil sampling locations throughout the site under consideration. This is accomplished by obtaining a plurality of soil samples having depth at various locations in the site. Samples may be collected by any suitable means known to those skilled in the art. In accordance with one preferred embodiment, samples are obtained using coring means such as Geoprobe coring, resulting in the extraction of soil cores encased in plastic tubes, e.g. Shelby Tubes, of 2–3 inches in diameter. The cores are taken from the site surface to the confining layer at each sampling location at the site. The number of sample points taken will vary depending upon the type of site and the contaminants involved. Preferably, sample points range from 5 to 30 locations per acre.

After collection of the soil samples, the vapor pressure of the soils is measured as a function of depth. In the case of core samples, the plastic covering of each core is cut laterally down the side and, using suitable instrumentation, the total vapor pressure is measured. In accordance with one preferred embodiment of this invention, the preferred instrumentation is a photoionization detector. Flame ionization detectors may also be employed; however, they may not always be suitable because they measure methane as well as organic contaminants. Other field sampling devices that are effective in measuring vapor pressure with depth can also be used. One such device is a cone penetrometer that is outfitted with suitable vapor pressure sensors or analytical equipment. Field vapor pressure data thus collected is then used to prepare a subsurface vapor pressure map.

The next step in the method of this invention involves determining the mobility of the contaminants. This is accomplished by locating those places within the soil core samples at which the vapor pressures are at a peak, removing a portion of the soil core samples encompassing said location and submitting the portion of the soil core to laboratory testing for contaminant mobility. Any test suitable for contaminant partitioning and determining release rates may be employed. Preferred methods for determining contaminant mobility include, but are not limited to, partitioning tests using the Synthetic Precipitation Leaching Procedure set forth in EPA Method 1312, water leach columns, serial dilution partitioning test, adsorptive resin test for measurement of release rates and rapid and slow release fractions, and short term biodegradation test.

Test Procedures

Water Leach Columns

About 300 grams of soil is placed into a column having a three-inch diameter. Approximately 5–10 pore volumes per day are passed through the column for about 15 days. Analyses include 1) benzene and naphthalene on filtered effluent water samples from the column; 2) BTEX, organic carbon, and total PAHs on the soil before and after leaching; and 3) TOC on initial and final samples of column leachate. Release rates can be estimated from leachate concentrations of contaminants. The rapid release and slow release fractions of contaminants can be estimated from soil residue data.

Resin Test for Rapid and Slow Release Fractions

Within six identical vessels, a slurry of soil sample, water and a quantity of hydrophobic molecular sieve resin is mixed over time in a flask. Over time, contaminants released from the soil into the water are irreversibly sorbed onto the resin. At various contact times, replicate flasks are sacrificed and the three phases (soil, water and resin) are separated and analyzed for contaminant concentrations. The contaminant release is generally biphasic, including a rapid release followed by a slow release as evidenced by the contaminant loading profile onto the resin with time. This method yields data on the Kg of contaminants that can be potentially released in a rapid-release mode from 1 $m^3$ of soil; this measurement is also called the "Release Index" of a soil. The Release Index is a measure of the severity of a contaminant source in terms of impact to groundwater. The resin method also yields data on the mass of contaminant in the slow release fraction.

EtOH/Water Extraction

In this test, the soil sample is extracted with approximately two liters of a water solution containing ethanol. The extract is filtered and analyzed for benzene and naphthalene. Soil solids remaining are also analyzed for benzene and naphthalene.

Synthetic Precipitation Leaching Procedure (SPLP)

The synthetic precipitation leaching procedure test is designed to estimate the fraction of the total contaminant concentration in a soil that can partition into water, simulating regional precipitation water quality under defined conditions.

The soil is placed into a Zero Headspace Extraction (ZHE) Vessel where it is contacted with water using vigorous shaking. The water is equal to about 20 times the weight of the soil. Following extraction, the liquid extract is separated from the solid phase by filtration through a 0.6 to 0.8 micron glass fiber filter. This filtrate is then analyzed for benzene and naphthalene.

Serial Dilution Partitioning Test (modified SPLP)

This procedure is conducted on a soil sample in accordance with U.S. EPA protocol SW 846 Method 1312. The original SPLP test, described hereinabove, is designed to estimate the fraction of the total contaminant concentration in a soil that can partition into water, simulating regional precipitation water quality under defined conditions. In this modified SPLP test, the soil sample is placed into a Zero Head Extraction Vessel where it is contacted with water using mechanical mixing. Four water-to-soil dilutions are applied in the test (nominally 100:1, 50:1, 20:1, and 4:1). The Zero Headspace Extraction Vessel is agitated to equilibrate the soils with water fractions for 24 hours. Following equilibration, the liquid extracts are separated from the solid phase by filtration through a 0.6 to 0.8 micron glass fiber filter. The filtrates are then analyzed for BTEX and naphthalene. The total amount of soil required for all the dilutions of this test is approximately 100 grams. Results from the test may then be plotted, from which it is possible to calculate the magnitude of the rapid release fraction and the slow release fraction.

Biodegradation Test

Aggressive aerobic biodegradation over a 7–10 day period removes the readily-soluble fraction that is rapidly released in soil. A soil sample is placed into an aerobic reactor that has been seeded with PAH degrading microorganisms. Aeration and mixing of the reactor are maintained for about ten days. Concentrations of the contaminants are measured in the soil before and after treatment. These concentrations may then be used to determine the relative fractions of rapid release and slow release fractions of benzene and PAHs.

Using the contaminant mobility tests described hereinabove, data on the partitioning and fractions of contaminants that are in the fast and slow release compartments in the soil are obtained. The results on the fast release fraction of a contaminant are then compared and correlated to the corresponding vapor pressures of these soils measured in the field and in the laboratory. Examples of such correlations are shown in plots shown in FIGS. 2–4. For a particular site, this comparison will establish the threshold PID where impact to groundwater is observed in the mobility measurements. PID measurements in the field can then be used to identify the spatial locations of soils that are problematic in terms of impact to receptors. These comparisons establish a screening threshold for PID that enable the site manager to determine which soils are problematic for releases of the contaminants and which soils are likely to impart a significant impact to receptors such as groundwater.

In cases where the contaminant of concern has a vapor pressure higher than most organic components of the NAPL and of the compounds that comprise the total vapor pressure, another test can be performed to ensure the conservative nature of the vapor pressure characterization approach. The vapor pressure characterization method of this invention assumes that total vapor pressure measurements are indicative of the release rates of the contaminant of concern. This assumption is correct as long as the ratio of the contaminant of concern to the total vapor pressure is constant or does not increase throughout the site relative to the most concentrated source area of the contaminant. This is at least theoretically likely because the fugacity (tendency to flee the NAPL/soil complex) of the contaminant of concern is often substantially higher than most of the components of the NAPL. As the NAPL ages, or as the NAPL flows across the site, losses of the contaminant of concern to the atmosphere or to the groundwater are likely to be higher than other NAPL contaminants. Thus, the fraction of the contaminant of concern in the vapor pressure exerted by NAPL/soil complexes is likely to be greatest at the most concentrated source. An important example of this situation is coal tar where the contaminant of concern is benzene but the vapor pressure is dominated by semi-volatile aromatic and light aliphatic compounds. To verify that the ratio does not increase compared to the most concentrated source zone, the following procedure may be employed.

First, samples are taken at the most concentrated source and at moderately contaminated areas of the site under consideration. Each sample is then placed in an enclosed container (standard weight of soil in a standard volume of enclosed container). After an equilibrium period, a PID reading is taken in the headspace of the container. In addition, a gas sample is taken from the headspace of the container and analyzed for benzene. The ratios of headspace benzene concentration to the PID value for each sample are then compared. The ratio values of the moderately contaminated soils should not be more than the ratio values measured at the most concentrated source locations.

Using the screening data obtained in accordance with the disclosed method, decisions can be made regarding the removal and/or treatment of contaminated soils.

EXAMPLE

In this example, vapor pressure screening in accordance with the method of this invention is employed to characterize the sources of mobile benzene contamination at a manufactured gas plant (MGP) site. Benzene is the contaminant of greatest concern because it is a carcinogen of the highest mobility in terms of solubility in water and in terms of vapor pressure. Vapor pressure measured in tar is primarily comprised of naphthalenes and light aliphatics with a minority of the vapor pressure represented by benzene. This example involves the characterization of a 3-acre MGP site.

Figure 2:
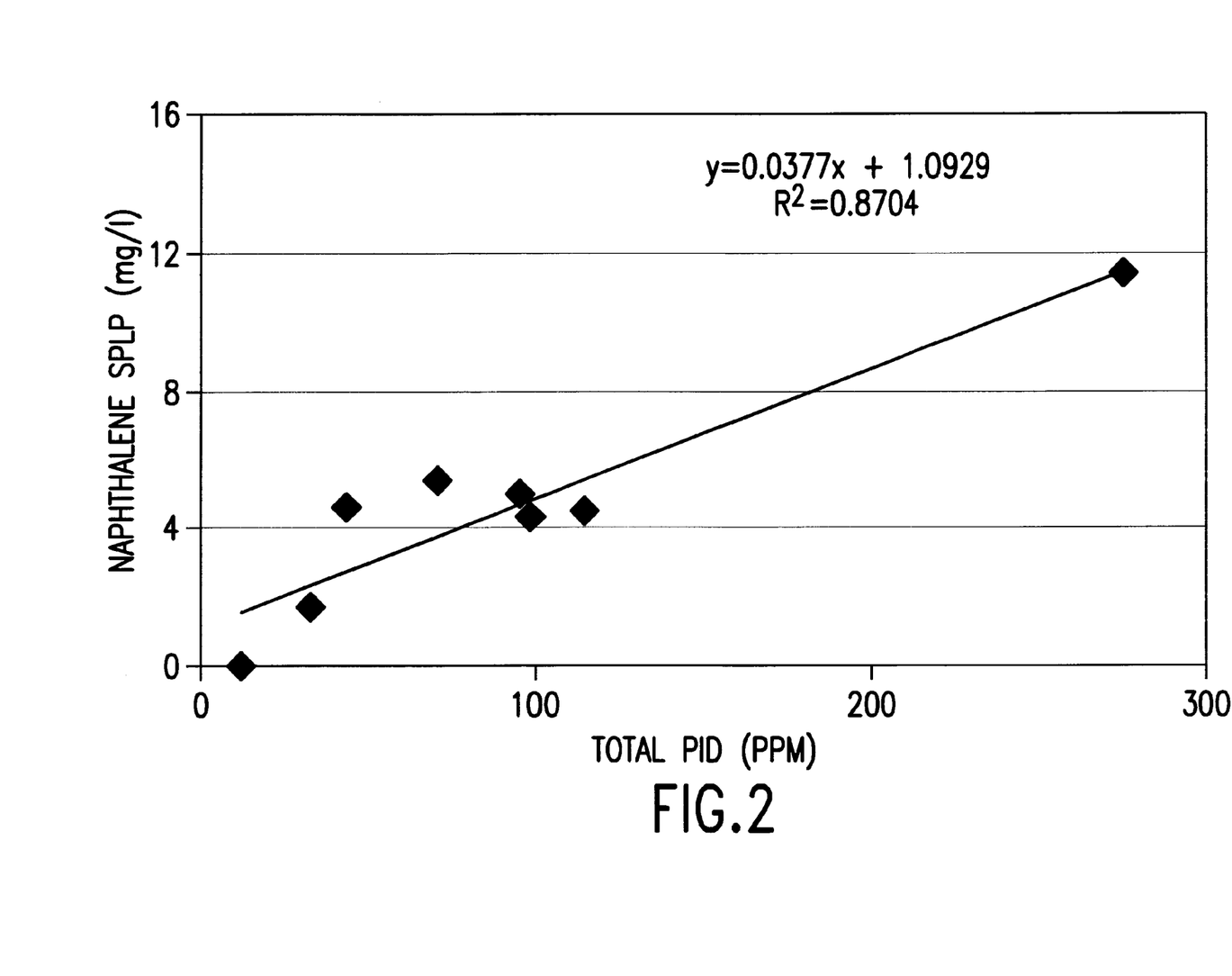
FIG. 2 is a diagram showing a plot of naphthalene SPLP versus total PID.
Figure 3:
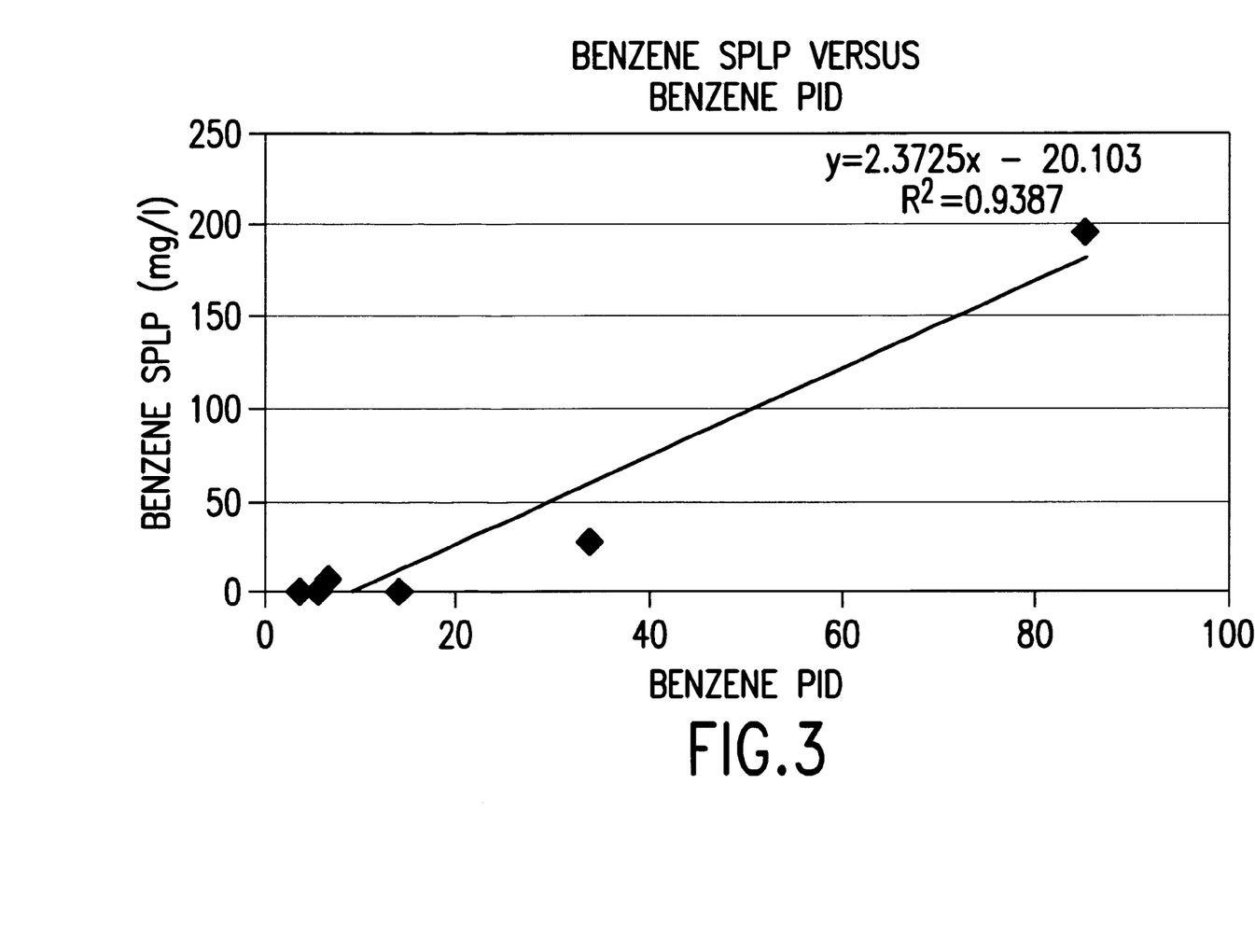
FIG. 3 is a diagram showing a plot of benzene SPLP versus benzene PID.
Figure 4:
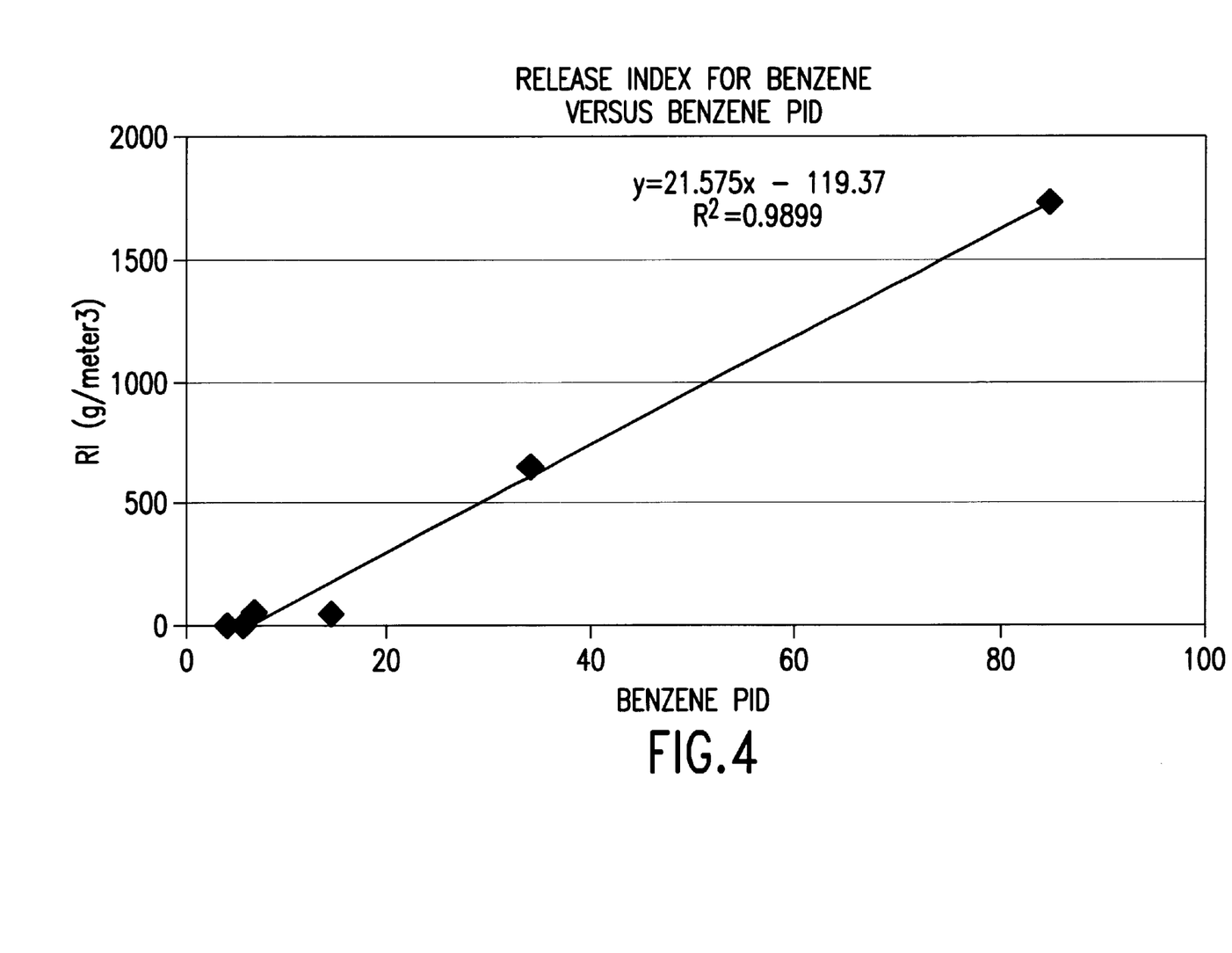
FIG. 4 is a plot showing the release index for benzene versus benzene PID.

At least 20 cores were taken at various locations (including source, near source and site perimeter locations) extending from the site surface to the confining layer of the groundwater table. The cores were split and a PID profile obtained as a function of depth at each location. At the peak PID depths and at 2 feet above and 2 feet below each peak, soil sections were taken from the cores. Each of the sections was placed into a sample bottle and screened and homogenized for mobility tests. An additional PID measurement of each of the screened soil samples in each of the containers was obtained using a portal arrangement that allows measurement of vapor pressures in the headspace of the container without losses of hydrocarbons to the atmosphere. Mobility tests were then conducted on each soil sample including the partitioning test, the serial dilution partitioning test and the resin test for determining the rapid and slow release fractions of benzene. Example plots of the SPLP partition test and the resin test are shown in FIGS. 2–4.

Comparisons of the vapor pressures (PIDs) with the mobility test results showed that PID values over a certain level represented a problematic release rate and represented an impact to groundwater that is unacceptable. The PID values below the certain level were not indicative of a problematic benzene source in soils or NAPL residues. Analysis of the sample bottle headspace of the most concentrated soil samples indicated that the benzene component of the vapor pressure in the headspace was approximately 2%. A similar analysis of lesser concentrated soil samples showed a benzene fraction of less than about 2% of the total organic vapor pressure. All of these tests comprised a fugacity calibration for the specific site.

Using this information, more detailed coring and PID measurements were carried out at the site to further identify locations of potential sources of rapidly released benzene. Benzene Release Index versus Benzene PID shows a close correlation, as shown in FIG. 4, allowing the PID device to be calibrated for the particular site under investigation. This allows the PID profile data to be converted to a spatial depiction of Release Index for each grid location of the site. This allows a more precise estimation of the location of the sources of benzene at the site. Vapor pressure characterization was also used to guide soil management actions taken at the site. The PID measurements were conducted, in part, during excavation of shallow soils to determine those soils needing to be aggressively treated and those soils that could be left in place. Some PID readings were taken from deep source areas to determine which soils required in-situ treatment with chemical and/or biological treatment to remove the majority of mobile benzene mass that comprises the source(s).

The method of this invention can be implemented quickly while expensive equipment and operators await answers as to which soils require aggressive management and which soils can be left on the site. The result of this approach is a more reliable, real-time classification of the soil which is suitable for determining what is truly a source and what is not a source of benzene or other contaminants in order to more effectively target soil volumes for removal and/or treatment. Savings of this approach to the 3-acre MGP site were realized in terms of more than a 50% reduction in soil volumes requiring active management.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. A method for identifying and characterizing contaminated sources in a site comprising contaminated soils and sediments comprising the steps of:

measuring vapor pressure at a plurality of subsurface soil sampling locations of said site, producing a plurality of subsurface vapor pressure measurements with depth;

mapping said plurality of subsurface vapor pressure measurements, resulting in generation of a subsurface vapor pressure map;

determining contaminant mobility;

identifying contaminants in fast release compartments and slow release compartments in said contaminated soils and sediments; and determining a fraction of said contaminants in said fast release compartments and said slow release compartments.

2. A method in accordance with claim 1, wherein said contaminant mobility is determined by identifying subsurface locations having a peak vapor pressure.

3. A method in accordance with claim 1, wherein said vapor pressure is measured by obtaining soil samples having depth at said plurality of subsurface soil sampling locations and measuring said vapor pressure at at least one depth within each of said soil samples.

4. A method in accordance with claim 3, wherein said soil samples are extracted as soil cores from said plurality of subsurface soil sampling locations.

5. A method in accordance with claim 4, wherein said soil cores extend in length from a surface of said site to a confining layer at each of said subsurface soil sampling locations.

6. A method in accordance with claim 1, wherein said measuring of said vapor pressure is carried out at said site.

7. A method in accordance with claim 1 further comprising removing from said contaminated soils and sediments said contaminants having a fast release rate while leaving behind said contaminants having a slow release rate.

8. A method in accordance with claim 1 further comprising quantifying a spatial mass distribution of rapidly released contaminant sources.

9. A method in accordance with claim 8, wherein said spatial mass distribution of said rapidly released contaminant sources is carried out by estimating a mass of rapidly released contaminants in each section of said site.

* * * * *